(12) United States Patent
Sullivan et al.

(10) Patent No.: US 8,694,084 B2
(45) Date of Patent: Apr. 8, 2014

(54) NON-CONTACT BIOPOTENTIAL SENSOR

(75) Inventors: Thomas J. Sullivan, San Diego, CA (US); Gert Cauwenberghs, San Diego, CA (US); Stephen R. Deiss, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 835 days.

(21) Appl. No.: 12/744,921

(22) PCT Filed: Nov. 26, 2008

(86) PCT No.: PCT/US2008/085051
§ 371 (c)(1),
(2), (4) Date: Oct. 25, 2010

(87) PCT Pub. No.: WO2009/070776
PCT Pub. Date: Jun. 4, 2009

(65) Prior Publication Data
US 2011/0043225 A1    Feb. 24, 2011

Related U.S. Application Data

(60) Provisional application No. 60/990,629, filed on Nov. 28, 2007.

(51) Int. Cl.
*A61B 5/04* (2006.01)
(52) U.S. Cl.
USPC ............... 600/522; 324/658; 204/403.02
(58) Field of Classification Search
USPC ............................ 324/658; 600/522
See application file for complete search history.

(56) References Cited

U.S. PATENT DOCUMENTS 3,477,421 A * 11/1969 Partridge .................. 600/522
4,331,158 A *  5/1982 Partridge .................. 600/522
(Continued)

FOREIGN PATENT DOCUMENTS

EP    0969477 A1    1/2000
EP    1487104 A2   12/2004
(Continued)

OTHER PUBLICATIONS

International Search Report for PCT/US2008/085051 issued Mar. 23, 2009.
(Continued)

*Primary Examiner* — Benjamin M Baldridge
(74) *Attorney, Agent, or Firm* — Eleanor M. Musick; Procopio, Cory, Hargreaves & Savitch LLP

(57) ABSTRACT

A capacitive sensor system including a sensing plate, an amplifier, and a switching circuit is described. The sensing plate is capacitively coupled to a body surface. A change in the electric potential on the body surface generates an electric field that induces change in the electric potential of the sensing plate. The sensing plate includes a sensing node positioned in the electric field for generating an input signal from the electric field. The sensing plate is not in contact with the body surface. The amplifier receives the input signal at the input port, amplifies the input signal and generates an output signal at the output port. The switching circuit is connected to the input port and a reference voltage. The switching circuit non-continuously closes a shunting path from the sensing node to the reference voltage to reset the voltage at the sensing node.

38 Claims, 6 Drawing Sheets

(56) References Cited

U.S. PATENT DOCUMENTS

| | | | |
|---|---|---|---|
| 4,412,546 A * | 11/1983 | Barthels | 600/522 |
| 4,417,590 A * | 11/1983 | Smith et al. | 600/544 |
| 4,751,471 A * | 6/1988 | Dunseath, Jr. | 330/53 |
| 5,018,523 A * | 5/1991 | Bach et al. | 607/2 |
| 5,331,966 A * | 7/1994 | Bennett et al. | 600/508 |
| 5,582,181 A * | 12/1996 | Ruess | 600/508 |
| 6,392,558 B1 * | 5/2002 | Schulmeyer et al. | 340/9.16 |
| 7,986,193 B2 * | 7/2011 | Krah | 331/44 |
| 8,000,789 B2 * | 8/2011 | Denison | 607/17 |
| 2003/0083714 A1 * | 5/2003 | Thompson et al. | 607/32 |
| 2003/0088279 A1 * | 5/2003 | Rissmann et al. | 607/5 |
| 2003/0105410 A1 | 6/2003 | Pearlman | |
| 2004/0152997 A1 | 8/2004 | Davies | |
| 2004/0228494 A1 * | 11/2004 | Smith | 381/67 |
| 2006/0085049 A1 | 4/2006 | Cory et al. | |
| 2007/0049845 A1 | 3/2007 | Fleischman et al. | |
| 2007/0175322 A1 * | 8/2007 | Baum et al. | 84/737 |
| 2007/0208235 A1 * | 9/2007 | Besson et al. | 600/301 |
| 2008/0079444 A1 * | 4/2008 | Denison | 324/679 |
| 2008/0100300 A1 * | 5/2008 | Williams | 324/458 |
| 2008/0157893 A1 * | 7/2008 | Krah | 331/177 R |
| 2009/0138059 A1 * | 5/2009 | Ouwerkerk | 607/5 |
| 2009/0255810 A1 * | 10/2009 | Ichino et al. | 204/403.02 |
| 2010/0219847 A1 * | 9/2010 | Douglas | 324/686 |
| 2011/0221452 A1 * | 9/2011 | Shyue | 324/658 |

FOREIGN PATENT DOCUMENTS

| | | |
|---|---|---|
| WO | 0213676 A2 | 2/2002 |
| WO | 2006007573 A1 | 1/2006 |
| WO | 2006061762 A2 | 6/2006 |
| WO | 2008135952 A1 | 11/2008 |

OTHER PUBLICATIONS

Supplementary European Search Report for 08855493.6 issued Dec. 7, 2012.

* cited by examiner

NON-CONTACT BIOPOTENTIAL SENSOR

RELATED APPLICATIONS

This application claims the benefit of U.S. Provisional Patent Application Ser. No. 60/990,629, filed Nov. 28, 2007, entitled "NON-CONTACT BIOPOTENTIAL SENSOR," which is hereby incorporated by reference in its entirety.

FIELD OF THE INVENTION

This invention relates to a low-noise, non-contact capacitive sensor system to measure electrical voltage signals generated by the body without direct contact with the body surface.

BACKGROUND

Electroencephalogram (EEG) and electrocardiogram (ECG or EKG) sensors measure the time-varying magnitude of electric fields emanating from the brain and heart, respectively, as a result of cellular activity within the organ. Currently available sensors for measurement of these electrical potentials require direct electrical contact with the skin, which can be achieved by using conductive gel between the sensor and the skin or by abrading the skin. While the gel satisfies the aim of making a good contact, there are several potential drawbacks. First, it can take up to an hour to apply the gel into EEG caps that use 256 sensors. In addition, the gel can diffuse through the hair to create shorts between sensors and can dry out over time, making long term recording very difficult. ECG sensors are often attached to the skin via an adhesive that requires that the attachment area be free of hair, i.e., shaved, and further that the skin area be lightly abraded to produce good contact. Removal of the sensors upon completion of the test is at best unpleasant and usually fairly painful.

There have been many attempts to use sensors that do not require gel, but still rely on dry contact with the skin. Generally, these approaches are limited to body areas with no hair. For example, the ICAP™ Release Meter System, described in U.S. Patent Publ. No. 2007/0048707, is a personal consumer product available from ICAP Technologies for stress management which holds an electrode in place against the user's forehead by way of an elastic headband. A hybrid approach, described in U.S. Pat. No. 6,510,333 of Licata, et al., avoids the need for direct application of gel while still relying on its conductive properties by using soft elastomeric bristles filled with conductive liquid or gels. A disadvantage is that the bristle pads can be relatively expensive to manufacture.

Early, non-contact biopotential sensors have had some success. Prance and co-workers have used low input-bias current amplifiers that yield low-noise operation at low frequencies. (See R. J. Prance, A. Debray, T. D. Clark, H. Prance, M. Nock, C. J. Harland, and A. J. Clippingdale, "An ultra-low-noise electrical-potential probe for human-body scanning", *Measurement Science and Technology*, vol. 11, pgs. 291-297, 2000; and C. J. Harland, T. D. Clark and R. J. Prance, "Electric potential probes—new directions in the remote sensing of the human body", *Measurement Science and Technology*, vol. 13, pgs. 163-169, 2002.) A drawback of such capacitively coupled electrical sensors is that parasitic charge builds up due to sensor drift and input bias offset currents. The conventional means for counteracting this drift involves including a conductive path to signal ground with a shunting resistor. The problem with such a scheme is that the high-valued resistor that is used contributes excessive amounts of thermal noise, contaminating the signal. U.S. Pat. No. 7,088,175 of Krupka describes a feedback circuit that continuously stabilizes the voltage at the input node of the amplifier. However, such circuits can also introduce noise and have relatively high power requirements.

Accordingly, what is needed is a gel-free non-contact sensor that avoids the need for contact with the skin altogether, is not limited to body areas with no hair, and further avoids the drift and noise problems of the prior art non-contact sensors.

BRIEF SUMMARY OF THE INVENTION

The present invention includes a capacitive biosensor system and method that provide a non-contact sensing plate that eliminates the need for contact with the skin surface and operates by capacitive coupling, and is capable of measuring electric fields through hair, clothing or other skin coverings. Drift and noise problems of the prior art are overcome by occasionally resetting the input node of the amplifier using a reset circuit. The timing and duration of the reset will depend on pre-determined conditions within the sensor such as direction and level of drift, or when voltage at the amplifier input exceeds a specified threshold.

In one embodiment, the inventive capacitive sensor system includes a sensing plate, an amplifier, collectively, the "basic capacitive sensor", and a switching circuit. The sensing plate is capacitively coupled to the body surface, such as human skin, either directly or through an intervening material such as hair, clothing or other skin covering. A change in the electrical potential on the body surface generates an electric field that induces change in the electrical potential of the sensing plate. The sensing plate includes a sensing node positioned in the electric field for generating an input signal from the electric field. The sensing plate is not in contact with the body surface. The amplifier includes an input port and an output port and is configured to amplify the input signal. The amplifier receives the input signal at the input port and amplifies the input signal to generate an output signal at the output port. The output signal is communicated to a readout device such as a printer or computer monitor to generate a visual indication of the detected signals. The output signal may in addition or in lieu of immediate display be communicated to a memory device for storage and subsequent transmission, viewing and/or processing. In order to avoid the build-up of parasitic charge, a switching circuit is connected to the input port of the amplifier and a reference voltage. The switching circuit non-continuously closes a shunting path from the sensing node to the reference voltage to reset the voltage at the sensing node.

In another embodiment, the build-up of parasitic charge at the input node of the amplifier is avoided by adding a switching circuit and a unity gain amplifier to the basic capacitive sensor in the capacitive sensor circuit. The switching circuit is connected to the input port of the amplifier and a reference voltage. The switching circuit includes at least one switching device and reset circuit including a plurality of capacitors. The capacitors are configured to generate activation voltage to turn on or activate the at least one switching device. The switching circuit is connected to the input port and a reference voltage where the switching circuit is configured to non-continuously close a shunting path from the sensing node to the reference voltage to reset the sensing node when the at least one switching device is turned on. The unity gain amplifier includes a first input port and a first output port. The first input port is coupled to the input port of the amplifier and is configured to generate a first output voltage at the first output port. The unity gain amplifier is coupled to one or more resistors where the one or more resistors are configured to pull the plurality of capacitors to the first output voltage when the at least one switching device is off.

Other features and advantages of the present invention will become more readily apparent to those of ordinary skill in the art after reviewing the following detailed description and accompanying drawings.

DETAILED DESCRIPTION OF THE INVENTION

A device for recording of electrical potentials on the surface of the human body is described. The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

Figure 1:
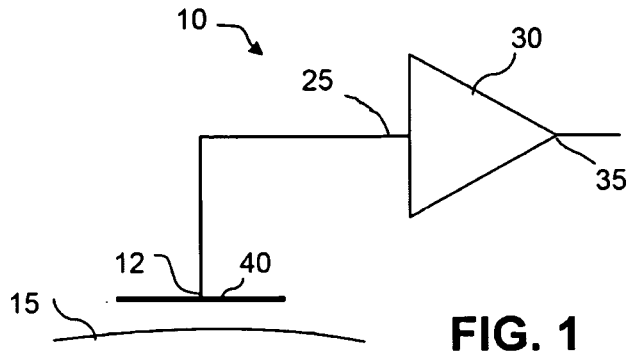
FIG. 1 illustrates one embodiment of capacitive sensor system for recording of electrical potentials on the surface of the human body according to the present invention.

FIG. 1 illustrates one embodiment of capacitive sensor system for recording of electrical potentials on the surface of the human body. The capacitive sensor system 10 includes a sensing plate 40 for capacitively coupling to a body surface 15, an amplifier 30 having an input port 25 and an output port 35. The capacitive sensor system 10 can be implemented as a Low-Noise, Non-Contact EEG/ECG Sensor, for example. The input port 25 includes a high impedance positive input and a low impedance negative input. The sensing plate 40 can be held close to the body surface 15. For example, the sensor can be one of a plurality of sensors distributed around the surface of a cap for the case of EEG. The sensing plate 40 is configured to function as a first plate of a sensing capacitor. The body surface 15 functions as the other "plate" of the sensing capacitor whose dielectric includes the medium in between the sensing plate 40 and the body surface 15. Some examples of the dielectric include air, hair, clothing, or the like. A change in the electrical potential at the body surface 15 generates an electric field that induces changes in the electrical potential on the sensing plate 40. The sensing plate 40 includes a sensing node 12 positioned in the electric field for generating an input signal to the input port 25 of the amplifier 30. The sensing plate 40 is not in contact with the body surface 15. The amplifier 30 receives the input signal via the input port, amplifies the input signal and outputs the amplified signal to the output port 35. The input port 25 of the amplifier 30 can include a high impedance input and a low impedance input. The amplifier 30 can be a voltage amplifier or an instrumentation amplifier. In one embodiment, the sensing plate 40 is connected to the high-impedance input of the amplifier 30 for readout. An amplifier input bias current exists at the input port 25 of the amplifier 30. The input bias current of the amplifier 30 is extremely small, but if left unattended will drive the high-impedance positive input node of the amplifier 30 toward one of the supply rails. To prevent driving the high-impedance positive input node of the amplifier 30 toward one of the supply rails, a reset or switching circuit that includes one or more switching devices is used.

Figure 2:
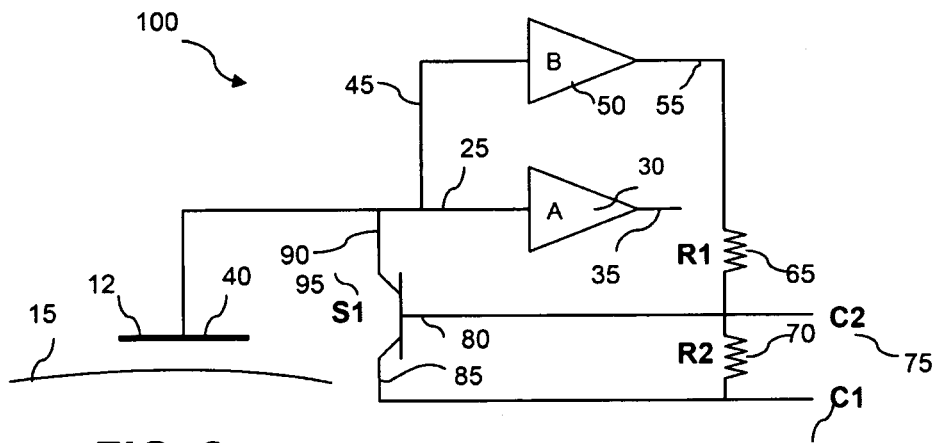
FIG. 2 illustrates a first alternative embodiment of the capacitive sensor system of FIG. 1, including a switching circuit.

In one embodiment, the capacitive sensor system 10 incorporates the switching circuit to non-continuously shunt a close a shunting path by using switching devices to occasionally briefly close a shunting path from the sensing node 12 to ground (or other reference) potential. An example of a simplified circuit that implements this principle is shown in FIG. 2 which illustrates one embodiment of the capacitive sensor system of FIG. 1, including a switching circuit. The capacitive sensor system 100 of FIG. 2 includes a sensing plate 40 for capacitively coupling to a body surface 15, an amplifier 30 having an input port 25 and an output port 35, a second amplifier 50 having a first input port 45 and a first output port 55, a switching device 95, capacitors 60 and 75 and resistors 65 and 70. The capacitive sensor system 100 can be implemented as a Low-Noise, Non-Contact EEG/ECG Sensor. Similar to the capacitive sensor system 10, amplifier 30 is used to amplify the input signal received at the input port 25 of the amplifier 30. The second amplifier 50 includes a first input port coupled to the input port 25 of the amplifier 30. The second amplifier 50, for example a unity gain amplifier, is configured to output a copy of the voltage at the input port 25 of the amplifier 30. Thus the second amplifier 50 is set to unity gain to form a copy of a voltage at the input port 25.

The input bias current of the amplifier 30 is extremely small, but if left unattended will drive the high-impedance positive input node of the amplifier toward one of the supply rails. A reset circuit or switching circuit which includes a switching device 95 is used to reduce the effect of the input bias current. The switching device 95 can be a transistor having a collector terminal 90 a base terminal 80 and an emitter terminal 85. The switching device 95, capacitors 60 and 75 and resistors 65 and 70 can be incorporated into the switching circuit. In one embodiment, the switching circuit is connected to the input port of the amplifier 30 and a reference voltage. The reference voltage can be ground. The switching circuit non-continuously closes a shunting path from the sensing node 12 to the reference voltage to reset the sensing node 12. Resetting the sensing node 12 includes resetting the voltage at the sensing node 12. Thus, the sensing node 12 is occasionally reset by the switching device (for example, a transistor or relay) that is closed to short the sensing node 12 to a known reference voltage. In one embodiment, the reference voltage is within the range of voltages included in the input common-mode voltage range of the amplifier 30. In one embodiment, to close a switch of the switching device 95, input capacitor 60 (C1) is connected to the reference voltage, while input capacitor 75 (C2) is connected to a voltage capable of turning on the switching device 95 (S1). After a brief time, capacitor 60 (C1) and capacitor 75 (C2) are disconnected from these voltages, thereby opening the switch and disconnecting the switching device 95. When the switching device 95 is disconnected, the resistors 65 (R1) and 70 (R2) have the effect of pulling capacitors 60 (C1) and 75 (C2) up to the voltage that is produced at the output port 55 of amplifier 50 (B). This pull-up method minimizes the current noise produced by the switching device 95 onto the sensing node 12.

Figure 3:
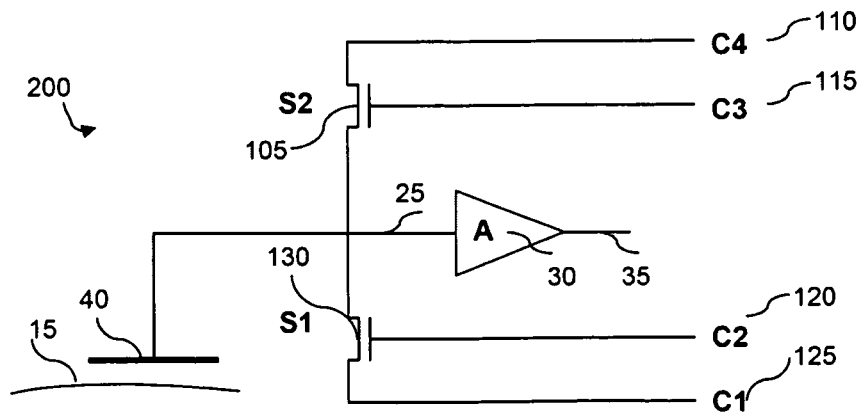
FIG. 3 illustrates second alternative embodiment of the capacitive sensor system of FIG. 1, including multiple switching devices.

In general, the switching that is used to reset or shunt the sensing node 12 can be accomplished in many different ways. FIG. 3 shows an alternative circuit that can be used. FIG. 3 illustrates one embodiment of the capacitive sensor system of FIG. 1, including multiple switching devices. FIG. 3 will be described with reference to FIG. 1 and FIG. 2 above. The capacitive sensor system 200 of FIG. 3 includes a sensing plate 40 for capacitively coupling to a body surface 15, an amplifier 30 having an input port 25 and an output port 35, a first switching device 130 coupled to a second switching device 105, capacitors 110, 115, 120 and 125. Similar to the capacitive sensor system 10, amplifier 30 is used to amplify the input signal received at the input port 25 of the amplifier 30 and to output the amplified signal at the output port 35 for display or further processing. In one embodiment capacitors 110 and 115 provide input to the second switching device 105 and capacitors 120 and 125 provide input to the first switching device 130.

In one embodiment, the first and the second switching devices, 130 (S1) and 105 (S2) can be Metal-Oxide Field-Effect Transistors (MOSFETs). The switching devices 130 (S1) and 105 (S2) can be switched on and off by controlling the input capacitors 110, 115, 120 and 125. In one embodiment, the switching partially resets the sensing node 12. Thus, the switching would not fully reset the sensing node to the ground (or reference voltage) potential, but rather move the sensing node voltage by a small amount towards ground (or reference voltage). While the switching devices 130 (S1) and 105 (S2) are not turned on (OFF state), the switching devices 130 (S1) and 105 (S2) could be biased with pull-up and pull-down resistors, as illustrated in FIG. 2 with respect to resistors 65 and 70. In one embodiment, the switching devices 130 (S1) and 105 (S2) are turned on one at a time periodically. In other embodiments, the input capacitors 125 (C1) and 110 (C4) are connected to the reference voltage, while input capacitors 120 (C2) and 115 (C3) are connected to a voltage capable of turning on the switching devices 95 (S1). The reference voltages at input capacitors 125 (C1) and 110 (C4) could be a power supply voltage, or other supplied voltage within the range of voltages included in the input common-mode voltage range of the amplifier 30 or near the middle of the amplifier's 30 common mode range (CMR). The duration and/or sequence of the times that the switching devices 130 (S1) and 105 (S2) are activated or turned on could be varied in relation to the direction and amount of voltage drift on the sensing node 12. For example, when the voltage at the sensing node 12 exceeds a given reference value, switching device 130 (S1) can be activated for a longer duration, and/or switching device 105 (S2) can be activated for a shorter duration, than otherwise. Conversely, when the voltage at the sensing node 12 reaches below a given reference value, switching device 130 (S1) could be activated for a shorter duration and/or switching device 105 (S2) activated for a longer duration. A similar scheme would modulate the sequence rather than duration of the switch activations, to preferentially close switching device 130 (S1) when the voltage at the sensing node 12 exceeds the reference level, and preferentially close switching device 105 (S2) otherwise. In other embodiments, a separate controller circuit or control module decides the period, pulse durations, and/or sequence of the switching similar to pulse-width modulator (PWM) and delta-sigma modulator (DSM) circuits, for example, that are used in switched power regulator and data conversion circuit design.

Figure 4:
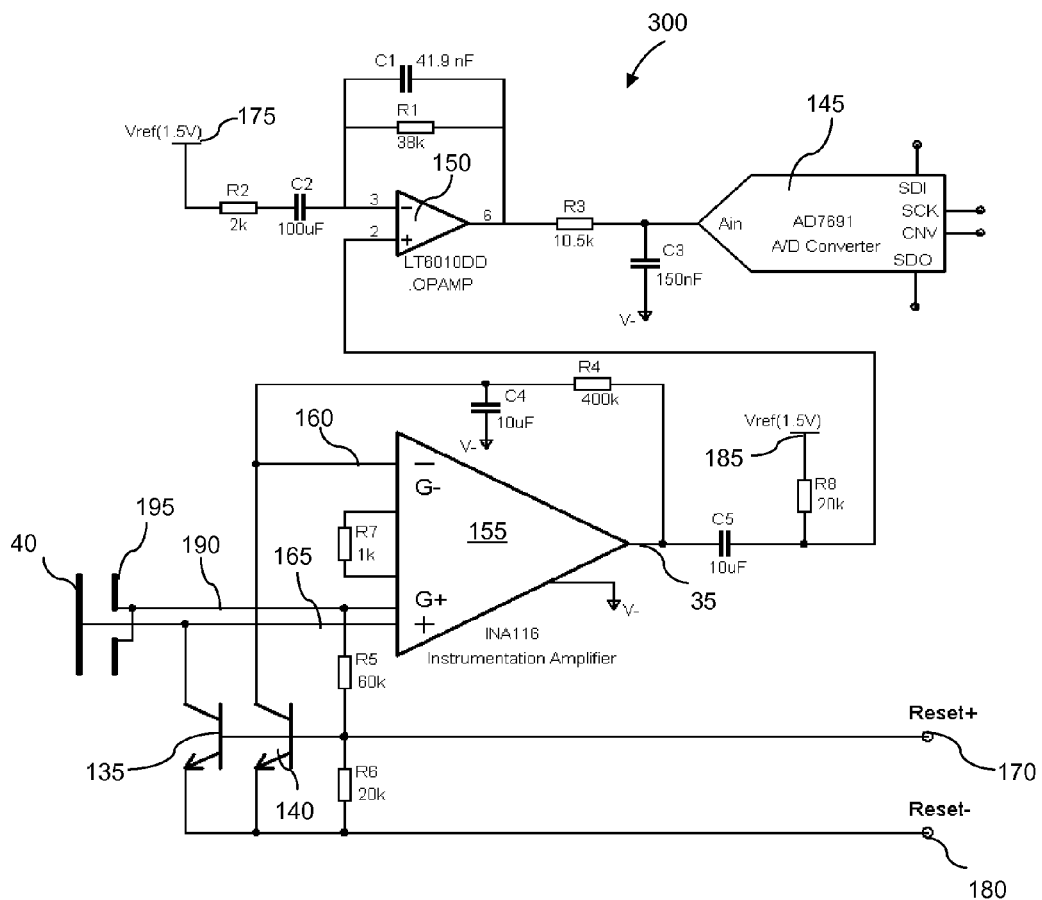
FIG. 4 illustrates a third alternative embodiment of the capacitive sensor system of FIG. 1, including multiple switching devices and a secondary amplifier for receiving level shifted output of the amplifier.

FIG. 4 illustrates one embodiment of the capacitive sensor system of FIG. 1, including multiple switching devices and a second amplifier for receiving level shifted output of the first amplifier. FIG. 4 is a specific example of the capacitive sensor system 300 including specific details such as examples of voltage, capacitance and resistance values. Particular implementations may vary from these exemplary details and still be contemplated to be within the spirit and scope of the present invention. The capacitive sensor system 300 of FIG. 4 includes a sensing plate 40 for capacitively coupling to the body surface 15, a first amplifier 30, a secondary amplifier 150, switching devices 135 and 140, capacitors C1 (41.9 nanofarad (nF)) to C5 (10 microfarad (μF)), resistors R1 (38 kilo ohm) to R8 (20 kilo ohm), reference voltages 175 (1.5 volts) and 185 (1.5 volts) and reset voltage references 170 and 180, and a level-shifter formed by capacitor C5 and resistor R8.

The signal on the body surface 15 (skin) capacitively couples to a metal plate, for example the sensing plate 40 illustrated in FIGS. 1, 2 and 3. The sensing plate 40 can be incorporated at the bottom of a printed circuit board (PCB), which is covered with solder mask for electrical insulation of the sensing plate 40 or the whole capacitive sensor system 300. A first amplification of the signal is accomplished by the first amplifier 30. In one embodiment, the first amplifier 30 is an instrumentation amplifier, configured for a gain of 50. Similar to the capacitive sensor system 10, amplifier 30 is used to amplify the input signal received at the input port 25 of the amplifier 30. The input port includes a negative amplifier input 160 and a positive amplifier input 165. In some embodiments, the instrumentation amplifier 30 may have a low input bias current of 3 femtoamp (fA) (typical) and an input current noise of 0.1 fA/$\sqrt{Hz}$ (typical).

The capacitive sensor system 300 also features a guard circuit that incorporates guard pin output or guard output 190, which follows the positive amplifier input 165 with a gain of 1. Implementation of the guard circuit that incorporates the guard output 190 is similar to the implementation of the unity gain amplifier 50 of FIG. 2. In one embodiment, the capacitive sensor system 300 implements a positive guard (for example, positive guard output 190) to support a guard ring around the positive amplifier input 165. The positive guard can also be used to drive a shielding metal plate 195 associated with the sensing plate 40, where the shielding metal plate 195 is configured to minimize electric field pick up from sources other than the body surface 15, (for example, the scalp). The shielding metal plate 195 may be implemented as an inner layer of metal on the printed circuit board (PCB) above the sensing plate 40. Because the guard circuit that incorporates the guard output 190 is actively driven to duplicate the voltage at the input port 25 of the amplifier 30, it avoids parasitic capacitance division of signal gain.

As previously described the reset or switching circuit may be used to prevent the input bias current of the amplifier from driving the positive amplifier input 165 toward one of the supply rails of the amplifier 30. The switching or reset circuit may include switching devices 135 and 140, resistors R5 (60 kilo ohms) and R6 (20 kilo ohms) and reset voltage references 170 and 180. The switching devices 135 and 140 (for example, transistors) are turned on by an external circuit including the reset voltage references 170 and 180, for example, when the voltage at the input port 25 is within the range of voltages included in the input common-mode voltage range of the amplifier 30. When the transistors 135 and 140 are off or are not driven, the base and emitter nodes, for example, of the transistors 135 and 140 are pulled up by the guard output 190. Pulling up the base and emitter nodes of the transistors 135 and 140 by the guard output 190 is done to minimize leakage currents (and especially the resultant current noise) from the transistors 135 and 140. The negative amplifier input 160 may be made to track the slowly changing positive input with the feedback loop consisting of resistor R4 (80 kilo-ohms) and capacitor C4 (100 micro-farad). This loop also serves to cut off input signals of frequencies below 1 Hz.

At the output port 35, the output of the instrumentation amplifier 30 is level-shifted and sent to the secondary amplifier 150. The secondary amplifier 150 can be an operational amplifier. A level-shifter is formed by capacitor C5 and resistor R8. This is a common high-pass filter which replaces the low frequency voltage of the amplifier output port 35 with the voltage Vref (1.5V). The higher frequency components of output port 35 pass through the level-shifter unaffected. This secondary amplifier 150 can be configured for a gain of 20, for example. The secondary amplifier 150 includes a second output port 6 and a second input port having a second negative input 3 and a second positive input 2. The second positive input 2 configured to receive the level shifted output of the instrumentation amplifier. A capacitor C2 (100 micro farad) is implemented at the second negative input 3 such that a zero is inserted at 1 Hz by C2, for example, to further cut off input signals of frequencies below 1 Hz. Two poles are implemented at 100 Hz by C1 (41.9 nano farad) reacting with R1 (38 kilo ohm) and C3 (150 nano farad) reacting with R3 (10.5 kilo ohm). This combination of capacitors and resistors complete a bandpass filter characteristic between 1 Hz and 100 Hz. Poles and zeros are properties of a transfer function representing the input signal for implementing a filter. In one embodiment, an analog to digital converter 145 is coupled to the secondary amplifier 150 via an interface, for example. The analog to digital converter 145 receives a secondary amplifier output signal that has been filtered by the bandpass filter implemented on the secondary amplifier 150. The analog to digital converter 145 is, for example, an 18 bit analog to digital converter that converts the secondary amplifier output signal to a stream of digital bits. The interface may optionally be daisy chained with other analog to digital converters 145 to reduce the number of wires in one or more capacitive sensor systems. The output of the analog to digital converter is connected to a data acquisition card on user interface such as a computer for display on a monitor or to a printer to produce a printed record of the measurement device for, for example, for device characterization.

In other embodiment, the total current required for the amplifier 30 is 1 ma from (a supply rail of) +5 volts (V) and −5 V power supplies. The secondary amplifier 150 and the analog to digital converter 145 may use single ended 3V supply and require 160 microamps total current. In some embodiments, the total power for the capacitive sensor system 300 is 10.5 milliwatt, which means that a hundred capacitive sensor systems can run for hours on a battery pack.

In addition to the examples described above, there are many other ways to implement a switching circuit that resets that critical sensing node 12. For example, the switches themselves can be transistors (bipolar, MOSFET, JFET, MESFET, etc.), relays (including traditional relays and micro-mechanical (MEMS) relays, mechanical switches, electronics switches, etc.) There may be as few as one switching device, or several switching devices. The reference voltages can be set to the middle of the amplifier CMR, the supply voltages, or other values. The reference voltages themselves can be varied by a feedback loop that searches for an optimal value. The switching can be performed when the input voltage or the voltage at the sensing node 12 is deemed close to the limits of the CMR, or at a regular interval. In either case, a controller can be used to determine which switching devices to activate, when to activate them, and the duration of activation. Alternatively, a human controller can determine when to reset the sensing node 12.

In the exemplary embodiment, the capacitive sensor is constructed from two custom printed circuit boards (PCBs) that are stacked one upon the other. The upper PCB, which is circular and about the size of a U.S. dime (~18 mm) includes the secondary amplifier 150, analog to digital converter 145 and some passive components (for example resistors R1, R2, R3 and capacitors C1, C2, C3). The bottom PCB, which is also circular and about the size of a U.S. quarter (~30 mm), holds the sensing plate 15, shielding plate 195, instrumentation amplifier 155 and switching devices 135 and 140 (e.g., transistors). In one embodiment, the bottom layer of the PCB is all metal covered with solder mask. In an alternative embodiment, all or a portion of the discrete components on the upper PCB can be incorporated into one or more integrated circuits which can be mounted directly on top of the lower PCB.

Figure 5A:
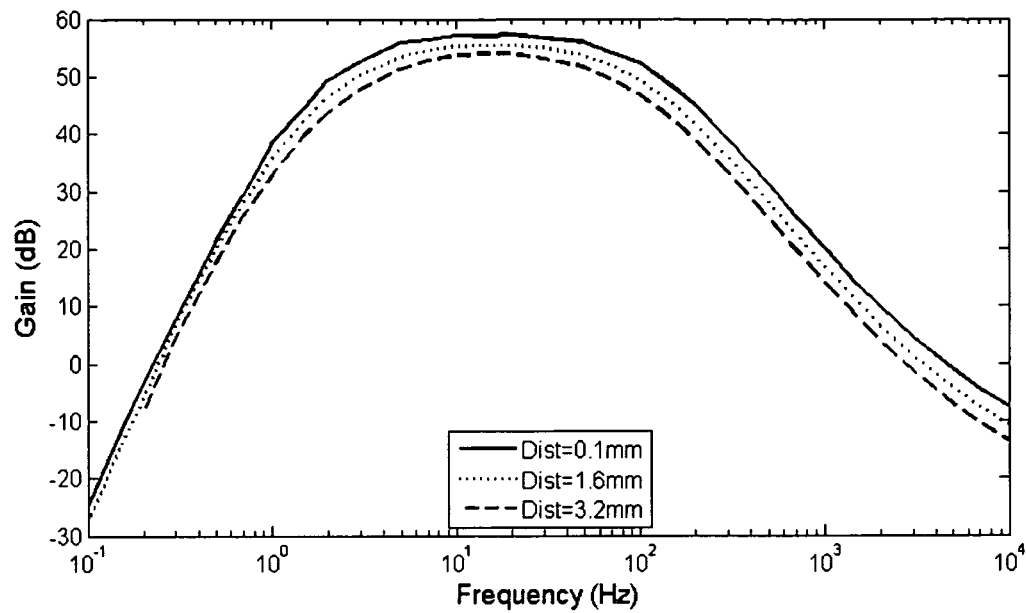
FIGS. 5A and 5B are graphs showing the effect of the separation distance between the sensing plate and the body surface on the input signal gain.
Figure 5B:
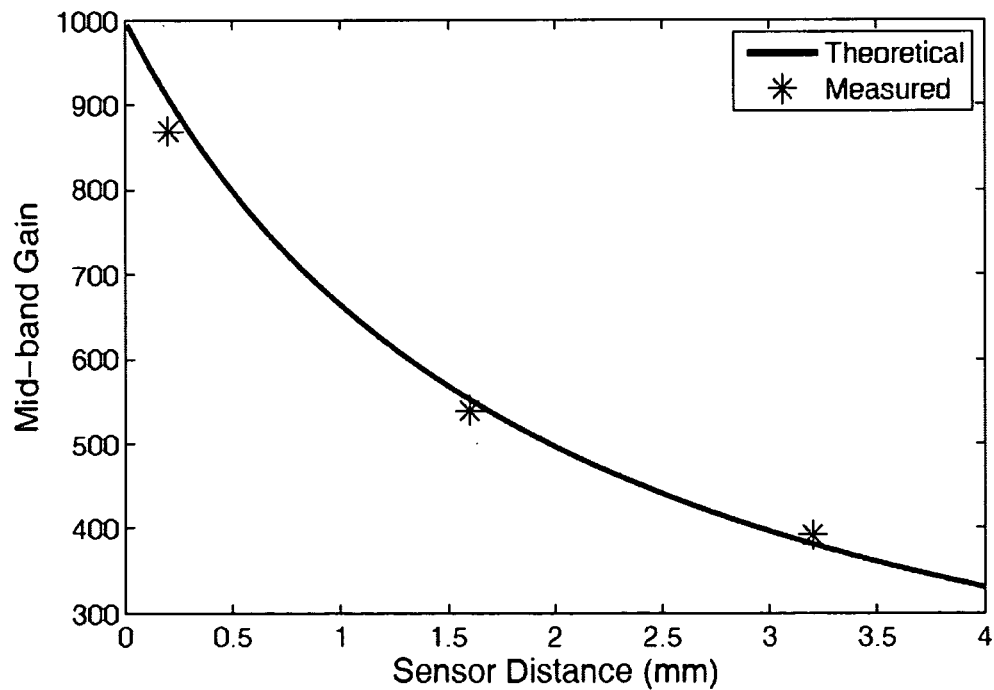

FIGS. 5A and 5B show exemplary results of the effect of the separation distance between the sensing plate and the body surface on the input signal gain. FIG. 5A and FIG. 5B are described with reference to FIGS. 1, 2, 3 and 4. FIG. 5A shows the measured gain of the input signal over a range of frequencies. The input signal is the signal generated by the sensing node 12 and received at the input port 25 of amplifier 30 or 155. The bandpass characteristic of the filtering between 1 Hz and 100 Hz as described with respect to FIG. 4 is evident in FIG. 5A. The 1 Hz cutoff may be steeper since there are three zeros acting there caused by the feedback loop of the instrumentation amplifier 155, capacitor C2 in the secondary amplifier 150 feedback, and the level-shifter formed by the capacitor C5 and the resistor R8. The two poles discussed previously with respect to FIG. 4 act at a frequency of 100 Hz.

In one embodiment, the input generated by the sensing node 12, for example the EEG input, can be modeled as a voltage source coupled into the capacitive sensor system 300 through a capacitor. The capacitance can be calculated as the area of the sensing plate 40 divided by the distance between the sensing plate 40 and the body surface 15 such as the scalp. Since there is also parasitic capacitance on the positive amplifier input 165 of the instrumentation amplifier 155 a capacitive voltage divider can be formed at the positive amplifier input 165 which reduces the input signal strength. FIG. 5B shows the gain for three different distances between the signal generator, for example the body surface and the sensing plate 40. As the distance is increased, the input coupling capacitance is reduced, as is the overall gain of the circuit. At a distance of 0.2 mm, the gain is 869, whereas it is 539 at 1.6 mm and 391 at 3.2 mm. The reduction in gain with distance is significantly larger when the active shield 195 is replaced with a passive ground shield. With active shield 195, the capacitive sensor system 300, (e.g., EEG/ECG sensor) is capable of operating over a wide range of separations as encountered with typical hair and clothing between the sensing plate 40 and body surface 15.

Figure 6A:
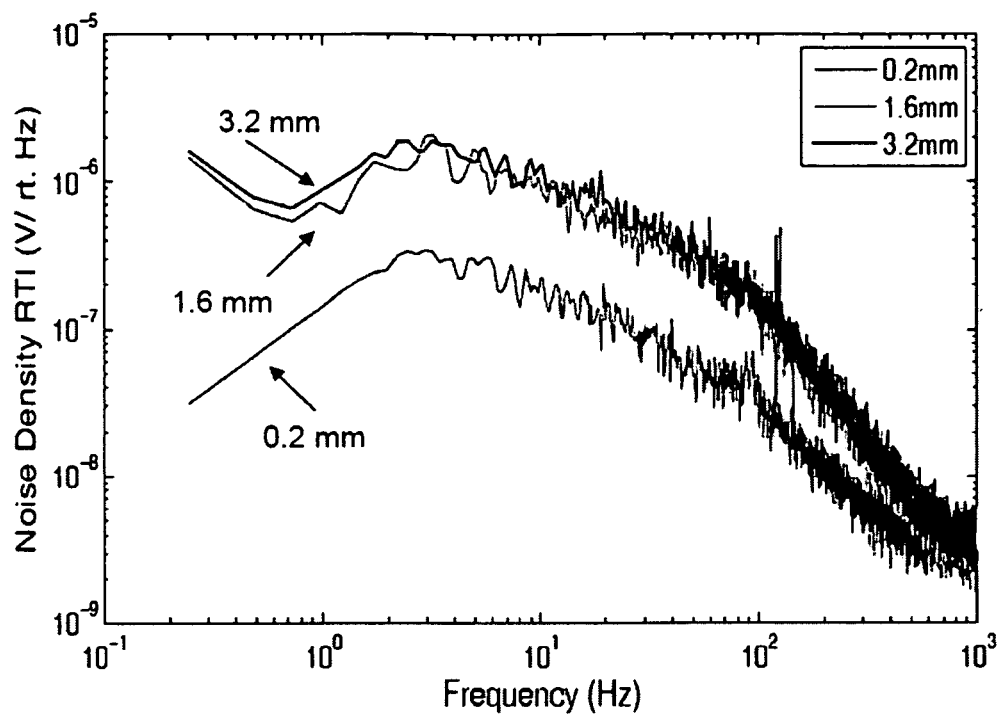
FIGS. 6A and 6B are graphs of the effect of sensor separation distance on the input referred noise.
Figure 6B:
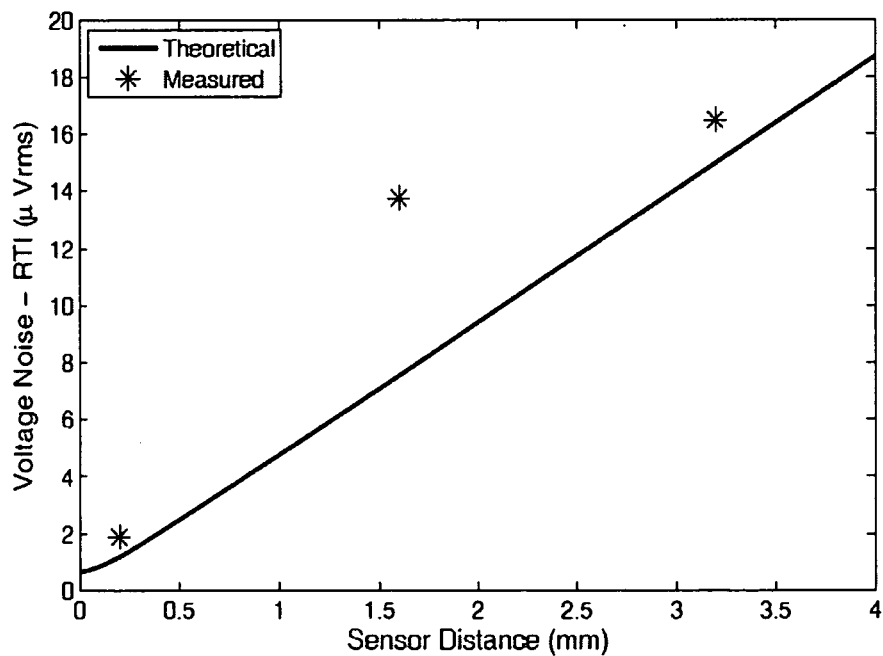

FIG. 6A and FIG. 6B are sample results illustrating the effect of sensor separation distance on input referred noise. FIG. 6A and FIG. 6B are described with reference to FIGS. 1, 2, 3 and 4. EEG sensor design such as the capacitive sensor system 300 requires an amplifier circuit with very low noise. The input signals being measured can be as low as tens of microvolts peak-to-peak, so noise levels below this are desirable. In some embodiments, the analog to digital converter 145 is not a significant source of noise since it converts a signal that has already seen a large gain (gain of 50 at the amplifier 155 and a gain of 20 at the secondary amplifier 150, for example) and it converts at 18-bit levels. The secondary amplifier 150 also does not contribute significant noise since it comes after the initial gain of 50 from the amplifier 155. In one embodiment, the calculated referred-to-input (RTI) voltage noise of the amplifier 155 in the frequency band from 1 to 100 Hz is about 0.66 microvolt root mean square (µVrms.) The RTI current noise of the instrumentation amplifier 155, though extremely small, is integrated by the capacitance seen at the positive amplifier input 165. Assuming a distance of 0.2 mm between the sensing plate 40 and the body surface 15, this current noise is converted to about 1 µVrms. In one embodiment, capacitive sensor system 300 features a circuit that incorporates guard pin output a guard output 190 and a guard input (not shown). Ideally, the guard input keeps the terminals of the switching devices 135 and 140 at the same voltage, keeping their leakage noise currents near zero. The resistor R4, though large, produces thermal noise that is not a significant factor because it is reduced by the feedback loop implemented on the amplifier 155. Thus, the total the expected RTI voltage noise is under 2.0 µVrms.

The measured noise density as a function of frequency is shown in FIG. 6A. With the sensing plate 40 that generates the input signal grounded, a spectral density estimate was measured at the output port of the amplifier 150 for distances between the sensing plate 40 and the body surface of 0.2 mm, 1.6 mm, and 3.2 mm. This resulted in a measured noise of 1.88 µVrms. The noise measured at the output port of amplifier 150 is then divided by the measured midband gain in FIG. 5A of the two amplifiers (for example, 794 or 58 dB). This process of referring the noise to the input (RTI) is done in order to compare the magnitude of the noise with the magnitude of the input signal of interest. The total noise in the frequency range of interest, 1-100 Hz, can be obtained by integrating the noise content shown in FIG. 6A within this range. FIG. 6B illustrates the results of this calculation for the three distances. FIG. 6B also shows the theoretically calculated noise using estimates of the noise contributed from the various elements in the circuit. For the distance of 0.2 mm between sensing plate 40 and the body surface 15, the measured total noise is 1.88 µVrms. As the separation distance between the sensing plate 40 and the body surface 15 increases, the coupling capacitance decreases. The current noise is then integrated to a larger voltage noise value.

The current noise is then integrated to a larger voltage noise value. FIG. 6B illustrates the theoretically calculated noise along with measurements at the same three distances used for the gain measurements of FIG. 6A. The input-referred rms noise is measured over the 1-100 Hz frequency band for the three separation distances, and compared with the theoretically expected noise. The theoretical curve accounts for the amplifier's 155 current and voltage input-referred noise, and for the capacitive division at the input port 25 of the amplifier 155.

Figure 7:
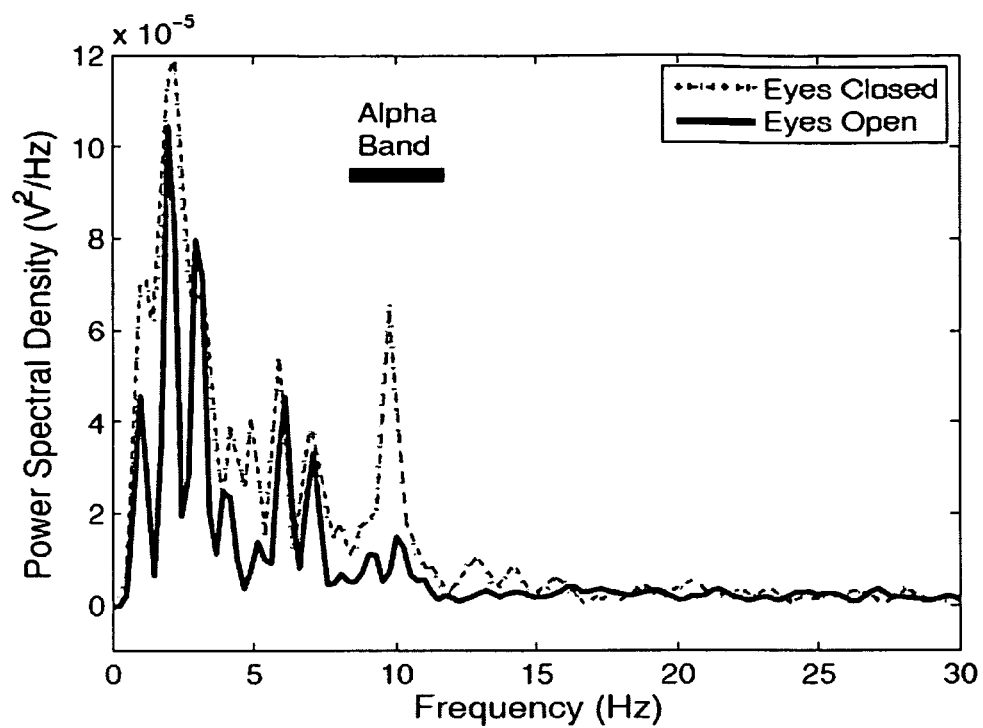
FIG. 7 is a graph of a power spectral density of input signals measured from two locations of the scalp.

FIG. 7 is a graph of a power spectral density of input signals measured from two locations of a test subject's head during testing of a prototype constructed according to the present invention. In one embodiment, sensing plates 40 are pressed against the subject's head using a headband, for example. The first sensing plate 40 is located in the back of the head (on top of the hair), while the second was located behind the ear to be used as a reference. The voltage difference between the two sensors was recorded as the subject first closed his eyes for 12 seconds then kept them open for the same amount of time. The power spectral densities of the data from these two blocks of time are shown in FIG. 7. Increased power in the alpha band of frequencies around 10 Hz can clearly be seen when the eyes are closed, as is commonly observed in EEG experiments, for example.

Figure 8:
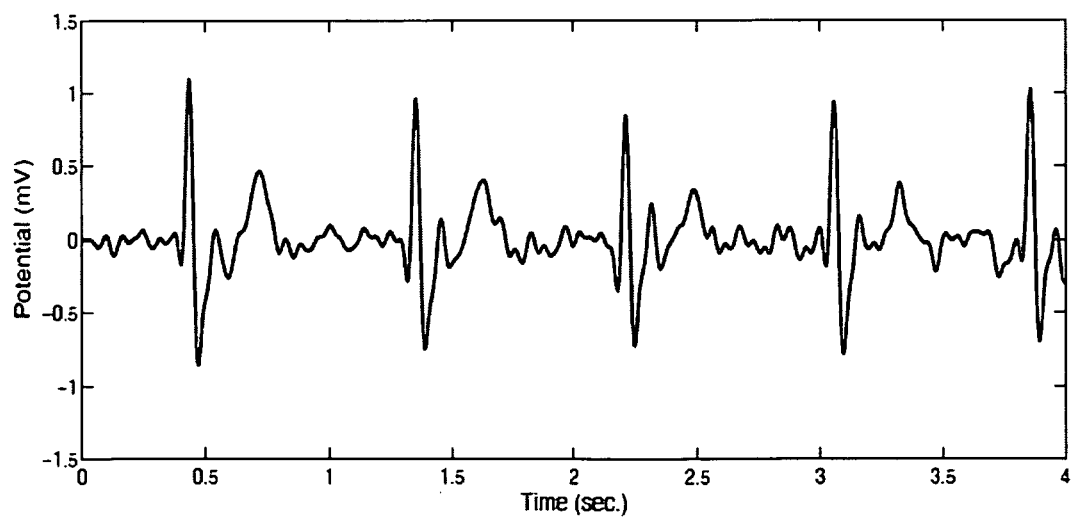
FIG. 8 is a graph of electrical potential versus time showing a typical ECG measurement taken through a T-shirt using the inventive biosensor.

FIG. 8 is a record of sample ECG voltage measured through a subject's T-shirt using sensors constructed according to the present invention. The graph illustrates the potential difference between two sensing plates 40 positioned near the heart. One of the sensing plates was located on top of the chest over the heart area and the second sensing plate was located on the side of the chest for use as a reference. Both sensing plates 40 were placed outside the subject's t-shirt. FIG. 8 is a 4 second record, which may be displayed on either or both of a monitor and a printer.

Figure 9:
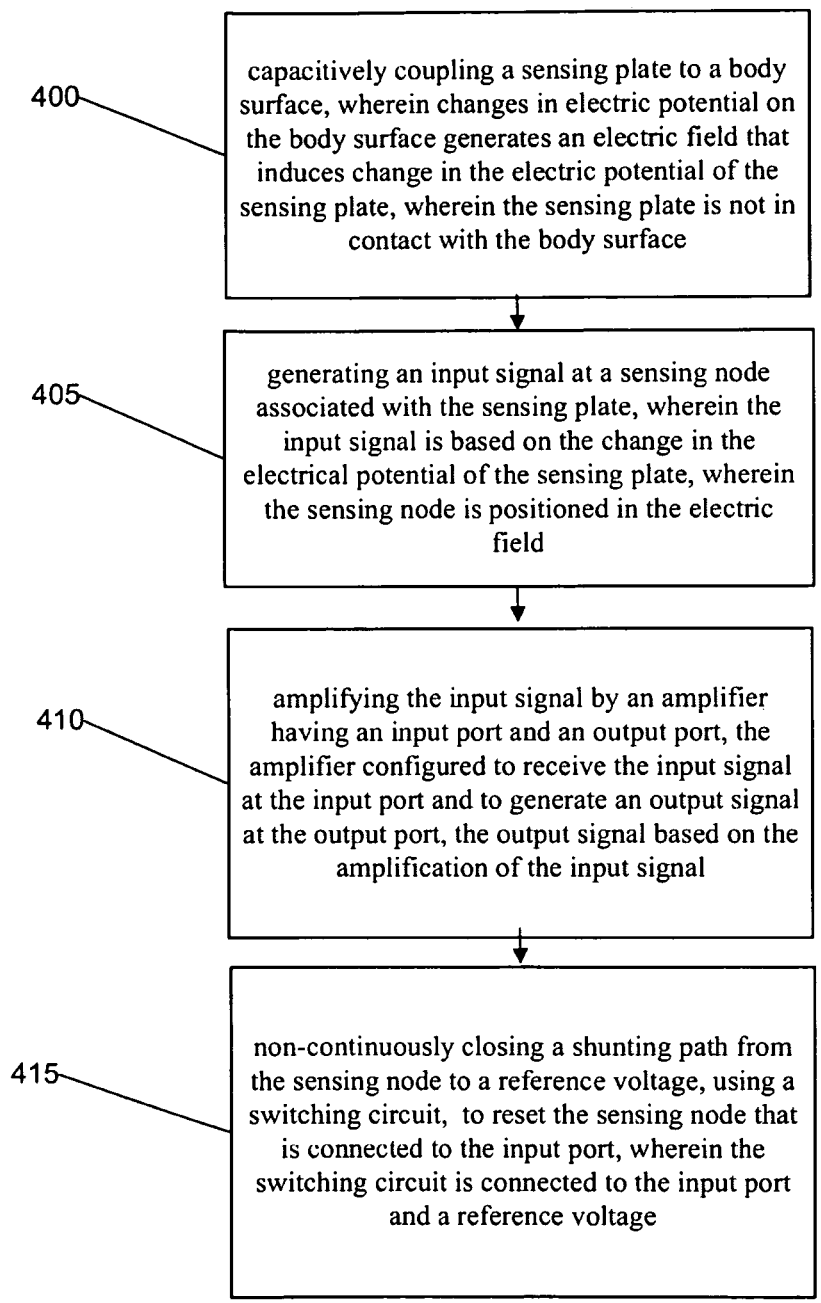
FIG. 9 illustrates a method of measuring an electric field using a capacitive sensor system according to an embodiment.

FIG. 9 illustrates one example of a method of measuring an electric field body surface using a capacitive sensor system according to an embodiment. The method can be implemented in the capacitive sensor system 100, 200 or 300 of FIGS. 2, 3 and 4. At block 400 the process starts with capacitively coupling a sensing plate 40 to a body surface 15. The change in electric potential on the body surface 15 generates an electric field that induces a change in the electric potential of the sensing plate 40. The sensing plate 40 is not in contact with the body surface 15. At block 405 an input signal is generated at a sensing node 12 associated with the sensing plate 40. The generated input signal is based on the change in the electrical potential of the sensing plate 40 where the sensing node 12 is position in the electric field. The process then continues to block 410 where the input signal is amplified by an amplifier having an input port and an output port. The amplifier is configured to receive the input signal at the input port and to generate an output signal at the output port where the output signal is based on the amplification of the input signal. Finally, at block 415, a shunting path is non-continuously closed, using a switching circuit, to reset the sensing node that is connected to the input port, wherein the switching circuit is connected to the input port and a reference voltage.

The systems and methods described above can be used for measurement of electroencephalographic (EEG) signals generated by the brain, for use in brain-computer interfaces. The systems and methods can also be used in the electrocardiography (ECG), for heart monitoring, and in electromyography (EMG), for recording of muscle activity. Unlike the majority of other EEG/ECG/EMG sensor designs, the capacitive sensor system and method described above is capacitive in nature and, hence, does not require physical or ohmic contact to the body surface such as the skin. Most of the existing sensors require electrical contact to the skin by application of conductive gel and/or by abrasive skin preparation, both of which are avoided in the present invention.

The capacitive sensor system and methods can be implemented in EEG caps such as medical diagnostic equipment, neuroprostheses, biofeedback, neuroimaging, brain-computer interfaces, and interactive computer games. The capacitive sensor system and method can be useful in EEG sensor interfaces to computer game software and for industrial applications such as monitoring of electrostatic build-up in electronics manufacturing.

The embodiments described herein accomplish the above features while contributing as little noise as possible to the sensing node 12. Only for the short duration of time that the switching devices are activated is any noise contributed. Furthermore, the switched operation allows replacement of the high resistance value with significantly lower resistance values, thus contributing lower thermal noise spectral density during activation.

The various embodiments described herein provide a means for combating the unwanted current at the critical input port of the amplifier with switching circuitry that occasionally resets or shunts the sensing node. As described above, the switching nature of the inventive circuits offers the advantage that less circuit noise is injected into the critical sensing node in a low power circuit.

Those of skill in the art will appreciate that the various illustrative modules and method steps described in connection with the above described figures and the embodiments disclosed herein can often be implemented as electronic hardware, software, firmware or combinations of the foregoing. To clearly illustrate this interchangeability of hardware and software, various illustrative modules and method steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module or step is for ease of description. Specific functions can be moved from one module or step to another without departing from the invention.

Moreover, the various illustrative modules and method steps described in connection with the embodiments disclosed herein can be implemented or performed with hardware such as a general purpose processor, a digital signal processor ("DSP"), an application specific integrated circuit ("ASIC"), field programmable gate array ("FPGA") or other programmable logic device, discrete gate or transistor logic, discrete hardware components, or any combination thereof designed to perform the functions described herein. A general-purpose processor is hardware and can be a microprocessor, but in the alternative, the processor can be any hardware processor or controller, microcontroller. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in computer or controller accessible on readable media including RAM memory, flash memory, ROM memory, EPROM memory, EEPROM memory, registers, hard disk, a removable disk, a CD-ROM, or any other form of storage medium including a network storage medium. An exemplary storage medium can be coupled to the processor so that the processor can read information from, and write information to, the storage medium.

In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein are exemplary embodiments of the invention and are therefore representative of the subject matter which is broadly contemplated by the present invention. It should be further understood that the scope of the present invention encompasses other embodiments and that the scope of the present invention is accordingly limited by nothing other than the appended claims.

REFERENCES

The teachings of the following references, which provide general background information, are incorporated herein by reference.

[1] J. C. Chiou, Li-Wei Ko, Chin-Teng Lin, Chao-Ting Hong, Tzyy-Ping Jung, "Using Novel MEMS EEG Sensors in Detecting Drowsiness Application," *IEEE Biomedical Circuits and Systems Conference*, 2006.

[2] A. Lopez and P. C. Richardson, "Capacitive electrocardiographic and bioelectric electrodes", *IEEE Transactions on Biomedical Engineering*, vol. 16, pg. 99, 1969.

[3] T. Matsuo, K. Iinuma, and M. Esashi, "A barium-titanate-ceramics capacitive-type EEG electrode", *IEEE Transactions on Biomedical Engineering*, vol. 188, pgs 299-300.

[4] R. J. Prance, A. Debray, T. D. Clark, H. Prance, M. Nock, C. J. Harland, and A. J. Clippingdale, "An ultra-low-noise electrical-potential probe for human-body scanning", *Measurement Science and Technology*, vol. 11, pgs. 291-297, 2000.

[5] C. J. Harland, T. D. Clark and R. J. Prance, "Electric potential probes—new directions in the remote sensing of the human body", *Measurement Science and Technology*, vol. 13, pgs. 163-169, 2002.

[6] R. Matthews, N. J. McDonald, I. Fridman, P, Hervieux, and T. Nielsen, "The invisible electrode—zero prep time, ultra low capacitive sensing. In *Proceedings of the 11$^{th}$ International Conference on Human-Computer Interaction*, Jul. 22-27, 2005.

[7] C. Park, P. H. Chou, Y. Bai, R. Matthews, and A. Hibbs, "An ultra-wearable, wireless, low power ECG monitoring system", *IEEE Biomedical Circuits and Systems Conference*, 2006.

[8] J. Errera and H. S. Sack, "Dielectric properties of animal fibers"

[9] T. Sullivan, S. Deiss, T. P. Jung, and G. Cauwenberghs, "A Low-Noise, Low-Power EEG Acquisition Node for Scalable Brain-Machine Interfaces", In *Proceedings of the SPIE Conference on Bioengineered and Bioinspired Systems III*, May 2-4, 2007.

The invention claimed is:

1. A biosensor system for measuring an electric field, said biosensor system comprising:
   a sensing plate capacitively coupled to a living body surface, wherein changes in electrical potential at the body surface generate an electric field that induces change in the electrical potential of the sensing plate, the sensing plate including a sensing node positioned in the electric field for generating an input signal from the electric field, the sensing plate separated from the living body surface by an intervening material;

an amplifier configured to amplify the input signal from the sensing node, the amplifier configured to receive the input signal at the input port and to generate an amplified output signal at the output port; and a switching circuit connected to the input port and a reference voltage, the switching circuit comprising at least one switching device configured to non-continuously close a shunting path from the sensing node to the reference voltage to reset the sensing node connected to the input port, wherein closing the shunting path from the sensing node to the reference node is performed in response to at least one of the input signal drifting away from the reference voltage by a predetermined amount, and a timing signal.

2. The biosensor system of claim 1, wherein the reference voltage is a ground.

3. The biosensor system of claim 1, wherein the reference voltage is within the range of voltages included in the input common-mode voltage range of the amplifier.

4. The biosensor system of claim 1, wherein the at least one switching device is a transistor.

5. The biosensor system of claim 1, further comprising a unity gain amplifier having a first input port coupled to the input port of the amplifier, the unity gain amplifier configured to output a copy of the voltage at the input port of the amplifier.

6. The biosensor system of claim 1, wherein the switching circuit further comprises multiple capacitors at least a first capacitor of the plurality of capacitors is connected to the reference voltage and at least a second capacitor of the plurality of capacitors is connected to an activation voltage capable of turning on the at least one switching device.

7. The biosensor system of claim 6, further comprising a unity gain amplifier having a first input port and a first output port, wherein the first input port of the unity pain amplifier is connected to the input port of the amplifier, wherein the first output voltage of the unity pain amplifier is a copy of the voltage at the input port of the amplifier, and wherein the unity gain amplifier is connected to one or more resistors, wherein the one or more resistors are configured to pull the plurality of capacitors to the first output voltage when the at least one switching device is off.

8. The biosensor system of claim 6, further comprising a guard output configured to pull up a base and an emitter node of the at least one switching device when the at least one switching device is off.

9. The biosensor system of claim 1, wherein the at least one switching device is turned on and off by controlling the inputs of a plurality of capacitors that are configured to supply activation voltage to the at least one switching device.

10. The biosensor system of claim 1, wherein the input port of the amplifier includes a high impedance input and a low impedance input.

11. The biosensor system of claim 1, wherein the sensing node is coupled to the high impedance input of the amplifier.

12. The biosensor system of claim 1, wherein the body surface is a living body surface.

13. The biosensor system of claim 1, wherein a dielectric of the sensing capacitor comprises the intervening material between the sensing plate and the body surface.

14. The biosensor system of claim 13, wherein the dielectric includes one of air, hair and clothing.

15. The biosensor system of claim 1, wherein the amplifier is a voltage amplifier.

16. The biosensor system of claim 15, wherein the sensing plate is connected to the high impedance input of the voltage amplifier.

17. The biosensor system of claim 1, wherein the sensing plate is configured to function as a first plate of a sensing capacitor and the body surface functions as a second plate of the sensing capacitor.

18. The biosensor system of claim 1, further comprising at least one reset circuit coupled to the switching circuit for turning on and turning off the at least one switching device.

19. The biosensor system of claim 1, wherein the at least one switching device includes a first switching device and a second switching device.

20. The biosensor system of claim 19, wherein the first switching device and the second switching device are activated one at a time periodically.

21. The biosensor system of claim 20, wherein the duration of the times that the first and the second switching devices are activated is based on the direction and amount of a voltage drift on the sensing node.

22. The biosensor system of claim 20, wherein the sequence in which the first and the second switching devices are activated is based on the direction and amount of a voltage drift on the sensing node.

23. The biosensor system of claim 1, wherein switching of the at least one switching device partially resets the sensing node.

24. The biosensor system of claim 23, wherein partial reset of the sensing node includes changing the voltage at the sensing node by an adapted to reduce a difference between the voltage at the sensing node and the voltage reference.

25. The biosensor system for of claim 1, wherein the timing signal is generated by a control module that controls one of the period, pulse duration and sequence of the switching.

26. The biosensor system of claim 1, wherein the reference voltage is varied by a feedback loop configured to optimize the reference voltage.

27. The biosensor system of claim 1, wherein the at least one switching device is activated when the voltage on the input signal approaches the limits of the range of voltages included in the input common-mode voltage range of the amplifier.

28. The biosensor system of claim 1, further comprising a guard output configured to follow the input port having a positive and a negative input with a gain of 1.

29. The biosensor system of claim 28, wherein the guard output is configured to support a guard ring around the positive input.

30. The biosensor system of claim 28, wherein the guard output is configured to drive a shielding metal plate associated with the sensing plate to minimize electric field pickup from sources other than the body surface.

31. A biosensor system for measuring an electric field, said biosensor system comprising:

a sensing plate capacitively coupled to a living body surface, wherein changes in electrical potential on the body surface generate an electric field that induces change in the electrical potential of the sensing plate, the sensing plate including a sensing node positioned in the electric field for generating an input signal from the electric field, the sensing plate separated from the living body surface by an intervening material;

an amplifier configured to amplify the input signal, the amplifier configured to receive the input signal at the input port and to generate an amplified output signal at the output port;

a switching circuit including at least one switching device and a reset circuit including a plurality of capacitors, the plurality of capacitors configured to supply an activation voltage to the at least one switching device to turn on or activate the at least one switching device, the switching circuit connected to the input port and a reference voltage, the switching circuit configured to non-continuously close a shunting path from the sensing node to the reference voltage to reset the sensing node connected to the input port when the at least one switching device is turned on, wherein the activation voltage is triggered by at least one of the input signal drifting away from the reference voltage by a predetermined amount and a timing signal; and a unity gain amplifier having a first input port and a first output port, the first input port coupled to the input port of the amplifier, wherein the unity gain amplifier is configured to generate a first output voltage at the first output port, and wherein the unity gain amplifier is connected to one or more resistors, wherein the one or more resistors are configured to pull the plurality of capacitors to the first output voltage when the at least one switching device is off.

32. The biosensor system of claim 31, wherein to turn on the at least one switching device, at least a first capacitor of the plurality of capacitors is connected to the reference voltage and at least a second capacitor of the plurality of capacitors is connected to a voltage capable of turning on the at least one switching device.

33. The biosensor system of claim 31, wherein turning on the at least one switching device include closing a switch of the at least one switching device.

34. The biosensor system of claim 33, wherein the switch is closed to short the sensing node to the reference voltage.

35. The biosensor system of claim 31, wherein the reference voltage is ground.

36. The biosensor system of claim 31, wherein the sensing plate is configured to function as a first plate of a sensing capacitor and the body surface functions as a second plate of the sensing capacitor.

37. The biosensor system of claim 31, wherein the first output voltage is a copy of the voltage at the input port of the amplifier.

38. A biosensor system for measuring an electric field generated at a surface of a living body, said biosensor system comprising:

a non-contact sensing plate capacitively coupled to the living body surface, the sensing plate comprising a sensing node positioned in the electric field for generating an input signal corresponding to the electric field;

an amplifier having an input port configured to receive the input signal and generate an amplified output signal; and a switching circuit connected to the input port and a reference voltage, the switching circuit comprising at least one switching device configured to non-continuously close a shunting path from the sensing node to the reference voltage to reset the sensing node connected to the input port, wherein the at least one switching device is responsive to an the activation voltage triggered by at least one of the input signal drifting away from the reference voltage by a predetermined amount and a timing signal.

* * * * *